(12) United States Patent
Gouda

(10) Patent No.: US 8,910,574 B2
(45) Date of Patent: Dec. 16, 2014

(54) MARK DETECTING DEVICE, ADJUSTMENT METHOD, AND PRINTING APPARATUS

(75) Inventor: Mitsunobu Gouda, Ibaraki (JP)

(73) Assignee: Ricoh Company, Limited, Tokyo (JP)

( * ) Notice: Subject to any disclaimer, the term of this patent is extended or adjusted under 35 U.S.C. 154(b) by 812 days.

(21) Appl. No.: 12/929,929

(22) Filed: Feb. 25, 2011

(65) Prior Publication Data
US 2011/0217053 A1  Sep. 8, 2011

(30) Foreign Application Priority Data
Mar. 6, 2010 (JP) .................................. 2010-049962

(51) Int. Cl.
| | | |
|---|---|---|
| B41F 1/34 | (2006.01) | |
| B41F 1/54 | (2006.01) | |
| G01N 15/00 | (2006.01) | |
| G01N 21/86 | (2006.01) | |
| G03G 15/00 | (2006.01) | |

(52) U.S. Cl.
CPC ................ *G01N 21/86* (2013.01); *G03G 15/00* (2013.01)
USPC .... 101/485; 101/484; 250/559.3; 250/559.44

(58) Field of Classification Search
CPC ............. B65H 2553/414; G03G 2215/00616; G03G 2215/0062; G03G 15/00; G01N 21/86; B41J 11/46
USPC ........ 101/484, 485; 250/559.3; 356/614, 620, 356/622; 399/308
See application file for complete search history.

(56) References Cited

U.S. PATENT DOCUMENTS

| | | | | |
|---|---|---|---|---|
| 6,201,256 B1* | 3/2001 | Kouchi et al. | ............ | 250/559.44 |
| 6,998,631 B2* | 2/2006 | Hirt et al. | ................. | 250/559.44 |
| 7,372,062 B2* | 5/2008 | Tanaka | ..................... | 250/559.45 |
| 7,903,526 B2* | 3/2011 | Kwak et al. | ................... | 369/103 |
| 2001/0042847 A1* | 11/2001 | Eisen et al. | ............. | 250/559.44 |
| 2002/0081132 A1* | 6/2002 | Miyamoto et al. | ............ | 399/384 |
| 2009/0080948 A1* | 3/2009 | Takei | ............................ | 399/308 |

FOREIGN PATENT DOCUMENTS

| | | | |
|---|---|---|---|
| JP | 2001522742 T | 11/2001 | |
| JP | 2005035064 * | 2/2005 | ............... B41J 11/42 |
| JP | 3680989 A | 5/2005 | |
| WO | WO-9924264 A1 | 5/1999 | |

OTHER PUBLICATIONS

JP 2002-187660 (Abstract Only).

* cited by examiner

*Primary Examiner* — Leslie J Evanisko
*Assistant Examiner* — Marissa Ferguson Samreth
(74) *Attorney, Agent, or Firm* — Harness, Dickey & Pierce, P.L.C.

(57) ABSTRACT

A mark detecting device detects a positioning mark on a transfer medium based on light that is emitted to and then reflected from the transfer medium. The mark detecting device includes a light emitting unit that emits light to a target position on the transfer medium; a light receiving unit that receives light reflected from the target position; and an adjusting unit that rotatably supports a detecting unit including at least one of the light emitting unit and the light receiving unit about a center of rotation, which passes through the target position, on the transfer medium and adjusts the rotation angle of the detecting unit with respect to the center of rotation.

10 Claims, 7 Drawing Sheets

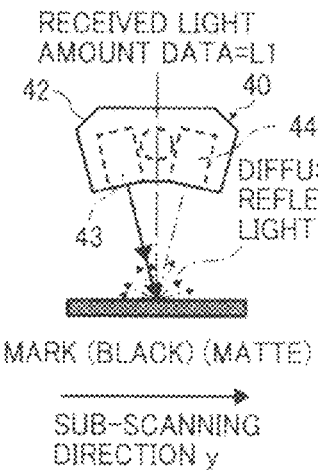

FIG. 4A1
RECEIVED LIGHT
AMOUNT DATA=L1

MARK (BLACK) (MATTE)
SUB-SCANNING
DIRECTION y

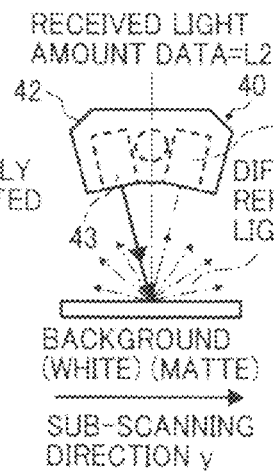

FIG. 4B1
RECEIVED LIGHT
AMOUNT DATA=L2

BACKGROUND
(WHITE) (MATTE)
SUB-SCANNING
DIRECTION y

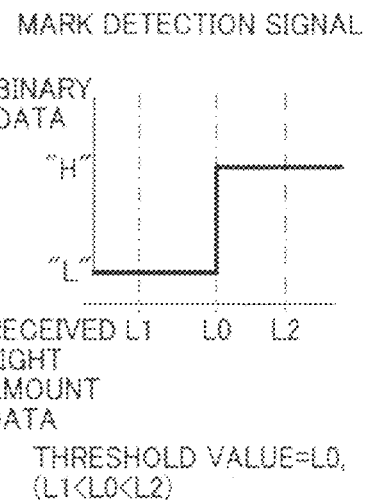

FIG. 4C1
MARK DETECTION SIGNAL

RECEIVED LIGHT AMOUNT DATA

THRESHOLD VALUE=L0, (L1<L0<L2)

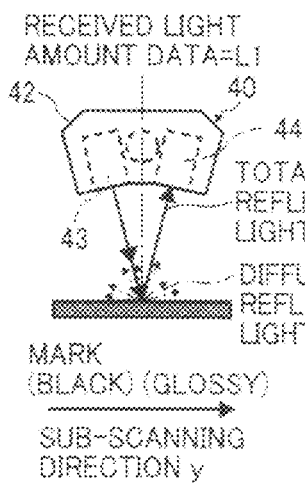

FIG. 4A2
RECEIVED LIGHT
AMOUNT DATA=L1

MARK (BLACK) (GLOSSY)
SUB-SCANNING
DIRECTION y

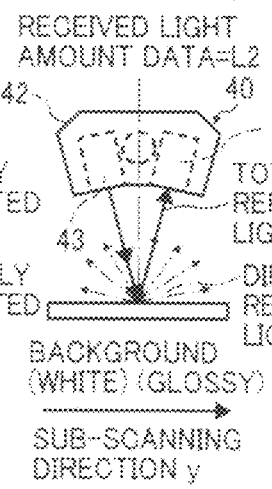

FIG. 4B2
RECEIVED LIGHT
AMOUNT DATA=L2

BACKGROUND
(WHITE) (GLOSSY)
SUB-SCANNING
DIRECTION y

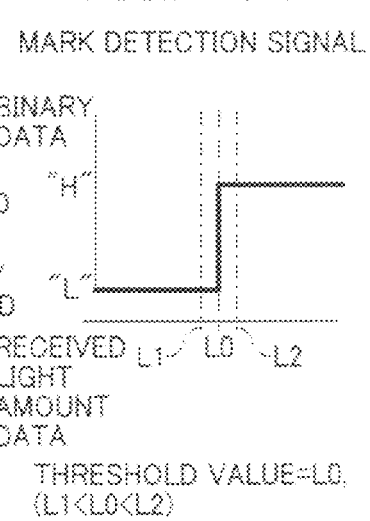

FIG. 4C2
MARK DETECTION SIGNAL

RECEIVED LIGHT AMOUNT DATA

THRESHOLD VALUE=L0, (L1<L0<L2)

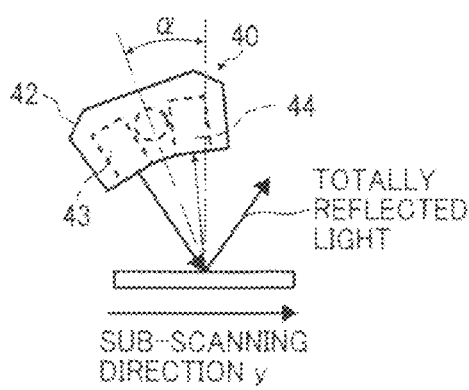

FIG. 4D

SUB-SCANNING
DIRECTION y

WHEN L1 AND L2 SATISFY DETERMINATION CONDITION L2−L1>△L1+△L2, IT IS POSSIBLE TO DISCRIMINATE MARK AND BACKGROUND.

WHEN L1 AND L2 DO NOT SATISFY DETERMINATION CONDITION L2−L1>△L1+△L2, IT IS DIFFICULT TO DISCRIMINATE MARK AND BACKGROUND.

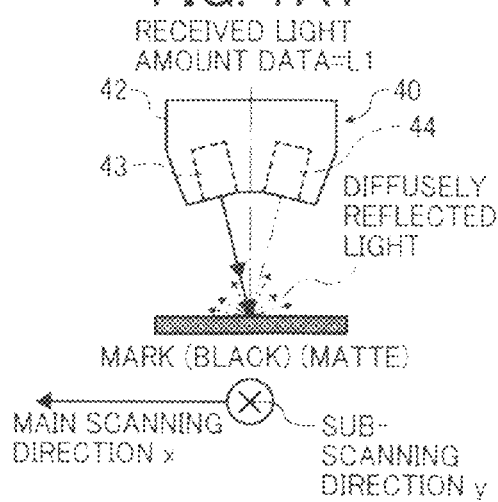
FIG. 7A1
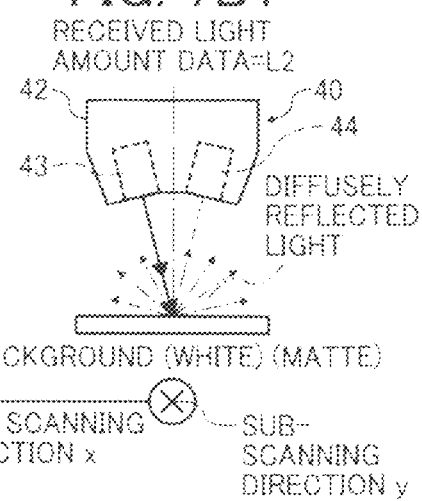
FIG. 7B1
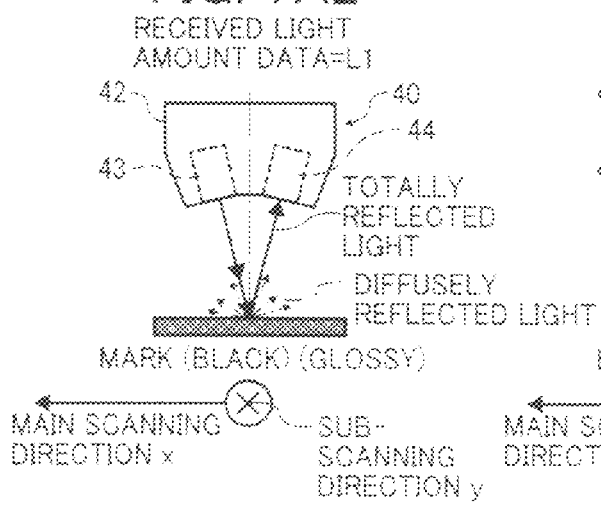
FIG. 7A2
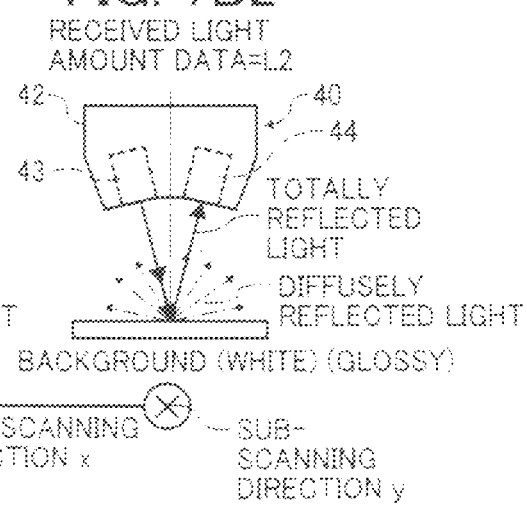
FIG. 7B2
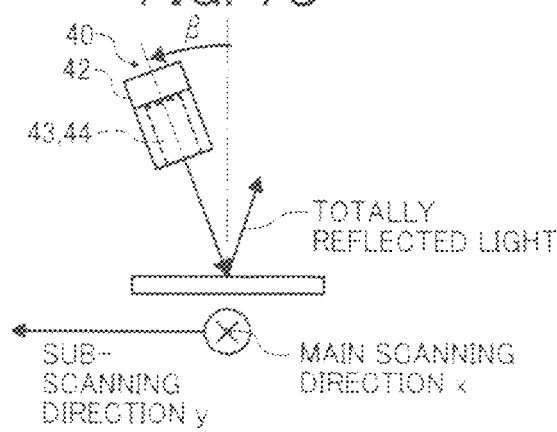
FIG. 7C

MARK DETECTING DEVICE, ADJUSTMENT METHOD, AND PRINTING APPARATUS

CROSS-REFERENCE TO RELATED APPLICATIONS

The present application claims priority to and incorporates by reference the entire contents of Japanese Patent Application No. 2010-049962 filed in Japan on Mar. 6, 2010.

BACKGROUND OF THE INVENTION

1. Field of the Invention

The present invention relates to a mark detecting device, an adjustment method, and a printing apparatus.

2. Description of the Related Art

As a printing system that forms images on both surfaces of a web, a printing system in which two printing apparatuses are connected in tandem has been widely known. In the printing system, a first printing apparatus P1 prints an image on the front surface of the web, the web having the printed front surface is reversed, and a second printing apparatus P2 prints an image on the rear surface of the web. In general, a strip-shaped sheet having feed perforations at both ends has been known as the web. After a printing process, the perforations at both ends of the sheet need to be cut out and discarded. Therefore, a printing system that can correspond to a web without a perforation has been widely spread.

In the printing system, when the web without feed perforations is transported, a friction transport method using a drive roller is used, unlike a feed perforation transport method using a tractor. Therefore, there is a variation in the amount of transport of the web due to a slip occurred between the drive roller and the web during friction transport or the tolerance of the drive roller. In addition, in tandem printing, the web transported to the second printing apparatus P2 is likely to be expanded or contracted after passing through the first printing apparatus P1. For example, in an electrophotographic printing apparatus, since toner is heated and fixed to the web, the web is thermally contracted.

A printing system has been proposed in which the second printing apparatus P2 detects a print position on the front surface and a speed control device corrects the print speed of the second printing apparatus P2 on the basis of the detection timing, in order to accurately align the print positions on the front and rear surfaces, regardless of a variation in the amount of transport of the web during friction transport or the expansion or contraction of the web during tandem printing (Japanese Patent No. 3680989).

In addition to double-side printing, when a pre-printed web is printed, the alignment between the print positions is performed. The color, position, and size of a pre-printed mark differ depending on web. Therefore, a mark detecting device has been proposed which is movable to any position in the horizontal direction (main scanning direction) and can detect the background and the pre-printed mark of any color using a reflective optical sensor, which is a representative example of a detecting device using a light emitting element composed of a plurality of red (R), blue (B), and green (G) light sources (Japanese Patent Application Laid-Open (Japanese Translation of PCT Application) No. 2001-522742).

It is preferable that the web printing apparatus align the print positions for various kinds of webs. However, in the mark position detection technique according to the related art, for example, when a glossy sheet is used as the web, in some cases, the detection accuracy of the mark is reduced and it is difficult to align the print positions. When using a normal non-glossy (matte) sheet, a sensor receives light that is diffusely reflected from the surface of the sheet, and the mark and the background are discriminated on the basis of a variation in the amount of light received. An example in which the reflective optical sensor detects the mark when a matte sheet is used as the web is shown in FIGS. 4A1 to 4C1. For example, when the sensor faces the mark (black), the amount of light received by the sensor is small. When the sensor faces the background (white), the amount of light received by the sensor is large. The sensor has a function of storing received light amount data L1 when facing the mark and received light amount data L2 when facing the background and a function of setting an intermediate value L0 as a threshold value. In the sensor, for example, when the amount of light received is more than L0, a detection signal becomes an "H" level, while when the amount of light received is less than L0, the detection signal becomes an "L" level. At the timing when the mark (black) passes through the sensor, the detection signal becomes an "L" level, and information indicating the passage of the mark is converted into an electric signal. In this way, it is possible to detect the mark.

In contrast, in the case of a glossy sheet, such as a coating sheet, the sensor receives light that is totally reflected from the surface of the glossy sheet, similar to specular reflection, in addition to diffusely reflected light. An aspect in which the reflective optical sensor detects the mark when a glossy sheet is used as the web is shown in FIGS. 4A2 to 4C2. In the case of the glossy sheet, the amount of light totally reflected is more dominant than the amount of light diffusely reflected. Since the amount of light received by the sensor during total reflection does not vary depending on whether light is reflected from the mark (black) or the background (white), the difference between the received light amount data L1 when the sensor faces the mark and the received light amount data L2 when the sensor faces the background is small. The detection distance between the sensor and the web vary depending on the thickness of the web used or a variation in transport to thereby vary the received light amount data. Therefore, in some cases, the variation ranges of the received light amount data L1 when the sensor faces the mark and the received light amount data L2 when the sensor faces the background exceed the threshold value L0, and it is difficult to discriminate the mark and the background. As a result, even when the mark passes through the optical axis of the sensor, it is difficult to detect the mark and determine the position. Therefore, a print error occurs and printing stops, which results in a reduction in the operation rate of the printing apparatus.

SUMMARY OF THE INVENTION

It is an object of the present invention to at least partially solve the problems in the conventional technology.

According to an aspect of the present invention, there is provided a mark detecting device that detects a positioning mark on a transfer medium based on light that is emitted to and then reflected from the transfer medium. The mark detecting device includes a light emitting unit that emits light to a target position on the transfer medium; a light receiving unit that receives light reflected from the target position; and an adjusting unit that rotatably supports a detecting unit including at least one of the light emitting unit and the light receiving unit about a center of rotation, which passes through the target position, on the transfer medium and adjusts the rotation angle of the detecting unit with respect to the center of rotation.

According to another aspect of the present invention, there is provided an adjustment method performed in a mark detecting device that detects a positioning mark on a transfer medium based on light that is emitted to and then reflected from the transfer medium. The adjustment method includes rotatably supporting a detecting unit including at least one of a light emitting unit that emits light to a target position on the transfer medium and a light receiving unit that receives light reflected from the target position about a center of rotation, which passes through the target position, on the transfer medium and adjusting the rotation angle of the detecting unit with respect to the center of rotation.

According to still another aspect of the present invention, there is provided a printing apparatus that includes a mark detecting device that detects a positioning mark on a transfer medium based on light that is emitted to and then reflected from the transfer medium; an image forming unit that forms an image on the transfer medium; a transport unit that transports the transfer medium to the image forming unit; and a transport control unit that changes transport speed of the transfer medium to the image forming unit by the transport unit on the basis of the positioning mark. The mark detecting unit includes a light emitting unit that emits light to a target position on the transfer medium; a light receiving unit that receives light reflected from the target position; and an adjusting unit that rotatably supports a detecting unit including at least one of the light emitting unit and the light receiving unit about a center of rotation, which passes through the target position, on the transfer medium and adjusts the rotation angle of the detecting unit with respect to the center of rotation.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2A shows the detection end 40 aiming at the front surface of a web W, and FIG. 2B shows the detection end 40 aiming at the rear surface of the web W;

FIGS. 4A1 to 4D are front views and side views illustrating the position of the detection end 40 shown in FIG. 1 facing the web and light reflected from the web W and diagrams illustrating a mark detection signal: FIG. 4A1 is a front view illustrating the detection of a mark on a matte web, FIG. 4B1 is a front view illustrating the detection of the background on the matte web, FIG. 4C1 shows a variation in received light amount data in the detection of the mark and the background, FIG. 4A2 is a front view illustrating the detection of a mark on a glossy web, FIG. 4B2 is a front view illustrating the detection of the background on the glossy web, FIG. 4C2 shows a variation in received light amount data in the detection of the mark and the background, and FIG. 4D is a side view illustrating the position of the detection end 40 where the detection end does not receive totally reflected light in the glossy web;

FIG. 6A shows the detection end 40 aiming at the front surface of a web W, and FIG. 6B shows the detection end 40 aiming at the rear surface of the web W; and FIGS. 7A1 to 7C are front views and side views illustrating the position of the detection end 40 shown in FIGS. 6A and 6B facing the web and light reflected from the web W; FIG. 7A1 is a front view illustrating the detection of a mark on a matte web, FIG. 7B1 is a front view illustrating the detection of the background on the matte web, FIG. 7A2 is a front view illustrating the detection of a mark on a glossy web, FIG. 7B2 is a front view illustrating the detection of the background on the glossy web, and FIG. 7C is a side view illustrating the position of the detection end 40 where the detection end does not receive totally reflected light in the glossy web.

DETAILED DESCRIPTION OF THE PREFERRED EMBODIMENTS

Features and advantages of the invention will become more apparent by describing in detail exemplary embodiments thereof with reference to the attached drawings.

First Embodiment

Figure 1:
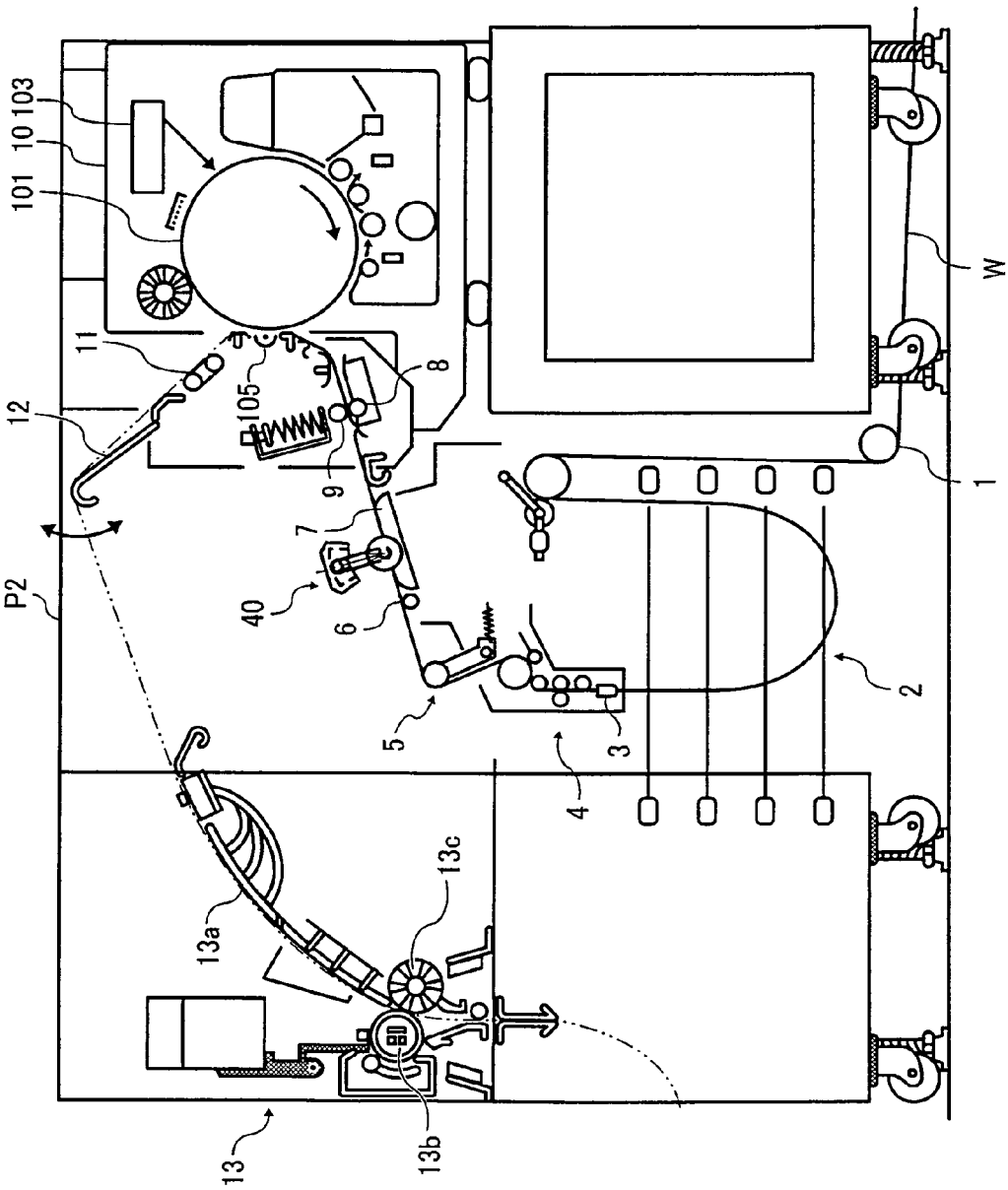
FIG. 1 is a longitudinal cross-sectional view illustrating the outline of a mechanism of a printing apparatus including a mark detecting device according to a first embodiment of the invention.

FIG. 1 shows the outline of a mechanism of a printer P2 according to a first embodiment of the invention. In a printing system including two web printing apparatuses connected in tandem, that is, a printer P1 (not shown) and a printer P2 according to this embodiment, the printer P1 prints a positioning mark on the front surface, and the printer P2 detects the positioning mark using a mark detecting device and aligns a print position. The positioning mark is formed in the vicinity of the head of each page and is used as a reference position when two printers are connected to each other and the image positions of the first printer P1 and the second printer P2 are aligned with each other. The second printer P2 detects the positioning mark formed by the first printer P1 and performs a control process of changing the speed of transport rollers 8 and 9 and a photosensitive drum 101 to accurately print an image on the second surface of a web W while aligning the image on the second surface with an image on the first surface.

In FIG. 1, W indicates a web. In general, the web W is a sheet of paper. The web W is fed from the first printer P1 (not shown) or a feed device (not shown), is guided to a guide roller 1 that is provided on a transport path so as to pass through the lower side of the printer P2, and is then transported to a web buffer mechanism 2. Then, the web W is transported to an image forming mechanism 10 through a guide member 3, a foreign material removing mechanism 4, a tension applying mechanism 5, a guide shaft 6, and a guide plate 7 by the transport rollers 8 and 9. The image forming mechanism 10 performs charging, exposure, developing processes to form a toner image on the photosensitive drum 101, and the toner image is transferred to the web W by a transfer device 105.

The web W transported from a transport belt 11 is transported to a fixing device 13 through a buffer plate 12. The web W reaching the fixing device 13 is preheated by a pre-heater 13a and is pinched and transported by a nip portion formed by a pair of fixing rollers composed of a heating roller 13b and a pressure roller 13c while being heated and pressed such that the toner image is melted and fixed to the web W.

Reference numeral 40 indicates a mark detection end of the mark detecting device according to this embodiment that detects the positioning mark formed on the web. The mark detection end 40 emits (radiates) light for detecting a mark to the web W and receives light reflected from the web W. In this embodiment, the mark detecting device includes the detection end 40 and a mark sensor 22 shown in FIG. 3.

Figure 3:
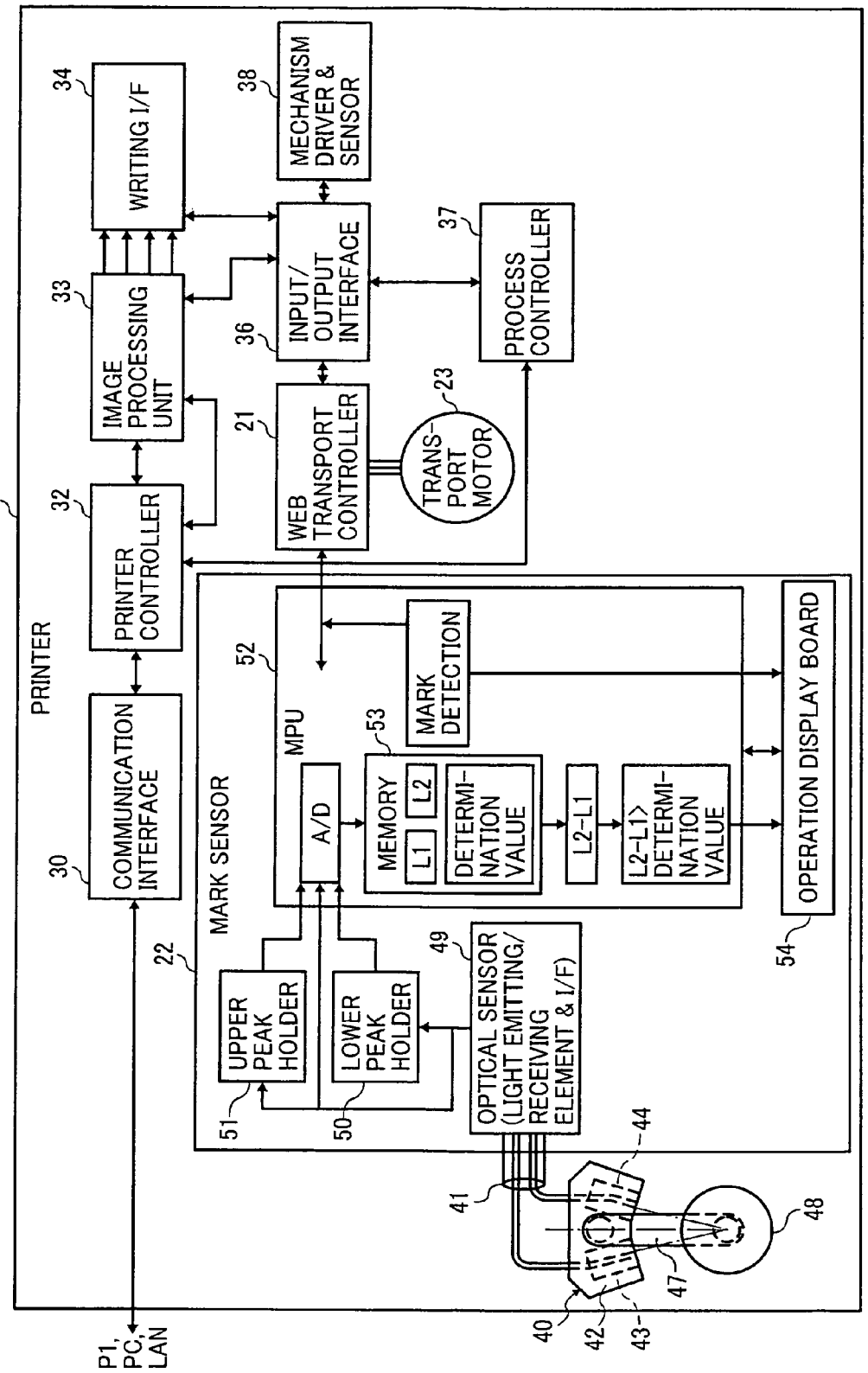
FIG. 3 is a block diagram illustrating the outline of the structure of an image processing and process control system of a printer P2 shown in FIG. 1.

An optical sensor 49 in the mark sensor 22 shown in FIG. 3 includes a light emitting element (LED) and a light receiving element (phototransistor). Light emitted, from the light emitting element is propagated through an optical fiber of an optical cable 41 and is then emitted from a light emission end 43 to the web W. Light reflected from the web W is incident on a light receiving end 44, is propagated through the optical fiber of the optical cable 41, and is then emitted to the light receiving element in the optical sensor 49. A detection signal (voltage) indicating the amount of light received by the light receiving element is converted into digital received light amount data by an A/D conversion function of an MPU (microcomputer) 52 and is then input to the MPU 52. In the stage of "the adjustment of an aiming angle" described later, the amount of light received is displayed on an operation display board 54. That is, the amount of light received is notified.

The MPU 52 of the mark sensor 22 binarizes the received light amount data with threshold value data (L0) to generate a mark detection signal (L: mark and H: background) shown in FIG. 4C1 or 4C2, and outputs the mark detection signal to the operation display board 54 and a web transport controller 21. The operation display board 54 displays a display lamp or a mark detection button on the display corresponding to the mark detection signal (L/H) so as to blink. The web transport controller 21 calculates whether the current web W is advanced or delayed on the basis of the deviation of the time when the mark detection signal L is generated from the reference time determined by the image forming sequence control of a process controller 37, corrects the rotation speed of a web transport motor 23 to correct the transfer speed of the web W, and aligns the print position of an image that is currently being formed with that of the image formed on the front surface or the rear surface of the web W. For example, if the time when the mark detection signal L is generated leads the reference time, the transfer speed of the web W is reduced. On the other hand, if the time when the mark detection signal L is generated lags the reference time, the transfer speed of the web W increases.

Figure 2A:
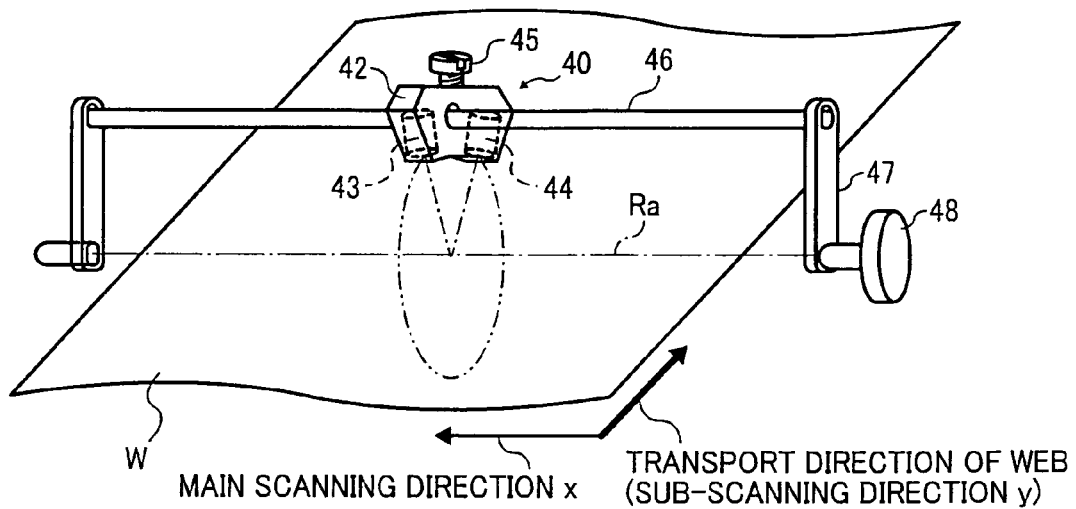
FIGS. 2A and 2B are enlarged perspective views illustrating the outline of an aiming angle adjusting mechanism that supports a detection end 40 shown in FIG. 1.
Figure 2B:
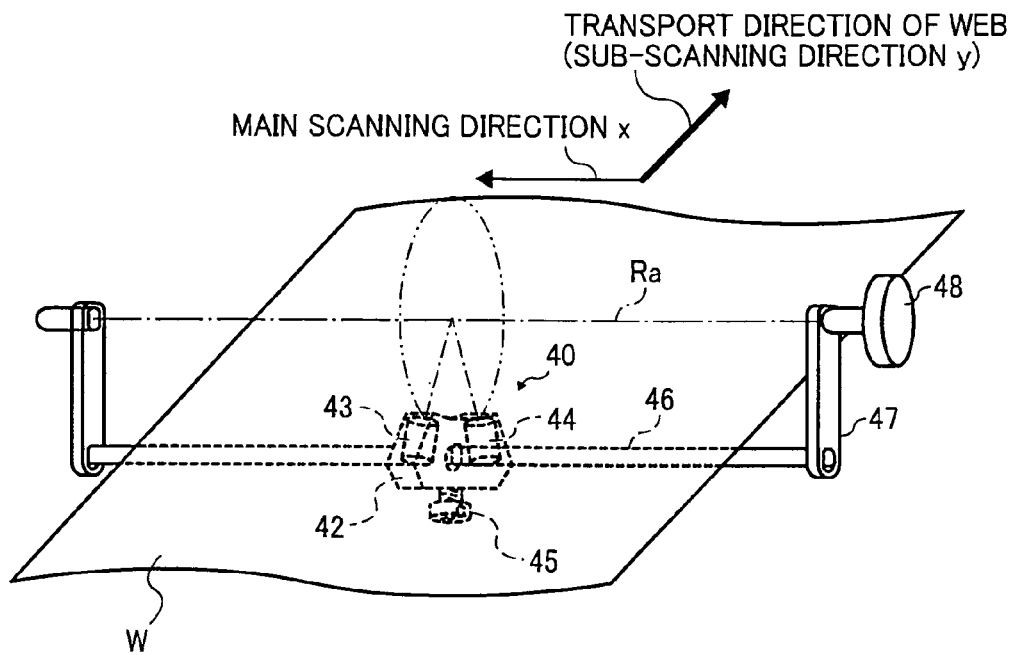

FIGS. 2A and 2B show the outline of the support structure of the detection end 40 shown in FIG. 1. In this embodiment, one end of a rotating arm 47 is rotatably supported by a printer mechanism frame (not shown) about a center line Ra of rotation of the level of the web W on a transport line in a transport direction y (sub-scanning direction) to the image forming mechanism 10. The center line Ra of rotation extends in a main scanning direction x perpendicular to the transport direction y. A knob 48 is coupled to the one end of the rotating arm 47 through an axial rod. A rotation angle dial is attached to the axial rod such that the operator can view the rotation angle, and an indicator is fixed to the axial rod such that the operator can read the rotation angle at the position of the indicator. The dial and the indicator are not shown. A fixing member (not shown) is provided in the axial rod of the knob 48. The fixing member is rotated when the operator applies torque, but stops the rotation of the axial rod while no torque is applied. After the operator rotates the knob 48 to adjust the rotation angle of the rotating arm 47 with respect to the center line Ra, the knob 48 maintains the adjusted rotation angle.

A guide bar 46 that is parallel to the main scanning direction x is supported by the free end of the rotating arm 47, and a slider 42 of the detection end 40 is mounted to the guide bar 46 such that it can slide in the main scanning direction x and is fixed to the guide bar 46 by a fixing screw 45. When the fixing screw 45 is loosened, the slider 42 can slide in the main scanning direction x. The guide bar 46 includes a flat cut surface extending over the entire length range, and the leading end surface of the fixing screw 45 comes into contact with the flat cut surface to prevent the rotation of the slider 42 with respect to the guide bar 46.

Web aiming lines of the light emission end 43 and the light receiving end 44 are perpendicular to the center line Ra. That is, the web aiming line is the radius of a circle having the center line Ra as its center. In this way, when the rotating arm 47 is rotated about the center line Ra, the web aiming lines of the light emission end 43 and the light receiving end 44 constantly aim at the center line Ra. Even when the knob 48 is rotated to adjust the rotation angle of the rotating arm 47 with respect to the center line Ra, web positions targeted by the light emission end 43 and the light receiving end 44 with respect to the web W do not vary. Therefore, the adjustment of the rotation angle does not cause a difference in the mark detection timing. That is, it is possible to change the incident angle of the optical axis (aiming line) of the light emission end 43 with respect to the web W without changing the detection position of the mark in the sub-scanning direction y.

Since the center line Ra of rotation of the light emission end 43 and the light receiving end 44 is at the level of the web W on the transport line, it is possible to rotate the rotating arm 47 about the center line Ra to detect the mark on the web W from the front side of the web W, as shown in FIG. 2A, and detect the mark on the web W from the rear side of the web W, as shown in FIG. 2B.

FIG. 3 shows the outline of the image processing system of the printer P2 shown in FIG. 1. A print command is transmitted from the first printer P1, a directly-connected personal computer (PC) or a PC connected to a LAN, Ethernet (registered trademark), or other networks to a printer controller 32 through a communication interface 30. The print command includes print conditions such as a sheet size and single-side/double-side printing, and image formation information. In general, the command from the first printer P1 is a special command related to synchronization control. The printer controller is also referred to as a system controller.

The image formation information included in the received print command is expanded to image data and is then output to an image processing unit 33. The image processing unit 33 converts the image data into image data suitable for printing by the image forming mechanism 10 shown in FIG. 1, expands the converted image data into an image memory of the image processing unit 33, magnifies the image data at a set magnifying ratio, cuts out a portion with a necessary size from the image data, and outputs the cut portion to a writing I/F 34, under the image forming process control of the process controller 37. The writing I/F 34 turns on or off a recording laser diode of a laser exposure device 103 or modulates the recording laser diode according to the image data.

Various kinds of sensors and actuators (an electric motor and a solenoid), which are mechanisms of the printer P2 shown in FIG. 1, are in a "mechanism driver & sensor" block 38. The mechanism driver & sensor block 38 is connected to an input/output interface 36, and the process controller 37 reads various kinds of sensor detection signals through the input/output interface 36 and drives the actuator of the image forming mechanism 10 through the input/output interface 36. In addition, the process controller 37 controls the operation timing and the signal input/output timing of the image processing unit 33 and the writing I/F 34 through the input/output interface 36. However, the web transport controller 21 controls the transport mechanism of the web W. The web transport controller 21 drives the transport motor 23 at a target speed with reference to the web transfer speed (target value) and the mark arrival reference timing given by, the process controller 37 and the mark detection signal (L) given by the MPU 52 of the mark sensor 22, and increases or decreases the drive speed of the transport motor 23 in correspondence with the advance or delay of the mark detection signal (L) with respect to the mark arrival reference timing so that the mark detection signal (L) is generated at the mark arrival reference timing.

The advantages of the adjustment of the incident angle of the optical axis (target line) of the light emission end 43 with respect to the web W will be described. When a matte sheet is used as the web and the light emission end 43 and the light receiving end 44 are arranged such that the optical axes thereof are symmetric with respect to the vertical line of the web, the incident angle of light incident on the web is equal to the reflection angle of light reflected from the web, as shown in FIG. 4A1. In the detection of both the mark and the background, as shown in FIGS. 4A1 and 4B1, the light receiving end 44 receives light diffusely reflected from the web. In the detection of the mark, since the intensity of the reflected light is low, the received light amount data L1 is at a low level, as shown in FIG. 4C1. In contrast, in the detection of the background, the received light amount data L2 is at a high level. Therefore, it is possible to binarize the received light amount data into the mark (L) and the background (H) with a threshold value L0. As a result, the reliability of the detection of the mark (L) is improved.

In contrast, when a glossy sheet is used as the web and the light emission end 43 and the light receiving end 44 are arranged such that the optical axes thereof are symmetric with respect to the vertical line of the web, the incident angle of light incident on the web is equal to the reflection angle of light reflected from the web, as shown in FIGS. 4A2 and 4B2. Therefore, the light receiving end 44 receives the totally reflected light of the web. In this case, both when the light emission end 43 and the light receiving end 44 face the mark on the web and when they face the background, the totally reflected light is dominant, and there is a small difference in the amount of light received between when the light emission end 43 and the light receiving end 44 face the mark and when the light emission end 43 and the light receiving end 44 face the background. Therefore, as shown in FIG. 4C2, the received light amount data L1 in the detection of the mark is close to the received light amount data L2 in the detection of the background detect and it is difficult to accurately perform binarization with the threshold value L0. That is, it is difficult to discriminate the mark from the detection signal.

Therefore, as shown in FIG. 4D, the rotation angle of the rotating arm 47 vertical to the plane of the web is changed by α degrees such that the optical axis of the light receiving end 44 deviates from the angle of the totally reflected light. With this, the diffusely reflected light is dominant in the amount of light received by the light receiving end 44 and there is a large difference in the amount of light received between when the light emission end 43 and the light receiving end 44 face the mark and when the light emission end 43 and the light receiving end 44 face the background. Therefore, when the glossy sheet is used, it is preferable to obliquely mount at least one of the light emission end 43 and the light receiving end 44 in order to easily discriminate the mark and the background. In this embodiment, the light emission end 43 and the light receiving end 44 are held by the slider 42 and the light emission end 43 and the light receiving end 44 are adjusted at the same angle. However, only one of the light emission end 43 and the light receiving end 44 may be rotated to adjust the angle.

Referring to FIG. 3 again, when the operator inputs an instruction to perform the mark detection test to the operation display board 54, the MPU 52 instructs the web transport controller 21 to perform test traveling. In response to the instruction, the web transport controller 21 drives the transport motor 23 to transport the web by a distance equal to or more than the period of the mark. During the transport, at least one mark passes immediately below the slider 42. An upper peak hold 51 of the mark sensor 22 holds the received light amount signal of the background, and a lower peak hold 50 holds the received light amount signal of the mark. The MPU 52 performs A/D conversion on the received light amount signals of the upper and lower peak holds 51 and 50 to obtain background received light amount data L2 and mark received light amount data L1, and writes the obtained data in a memory 53. The memory 53 stores a determination value which is a default value.

Then, the MPU 52 calculates a difference L2−L1 between the mark received light amount data L1 and the background received light amount data L2 and compares the difference with the determination value. An example of a process of determining whether the difference L2−L1 between the received light amount data items L1 and L2 is appropriate is as follows.

Figure 5A:
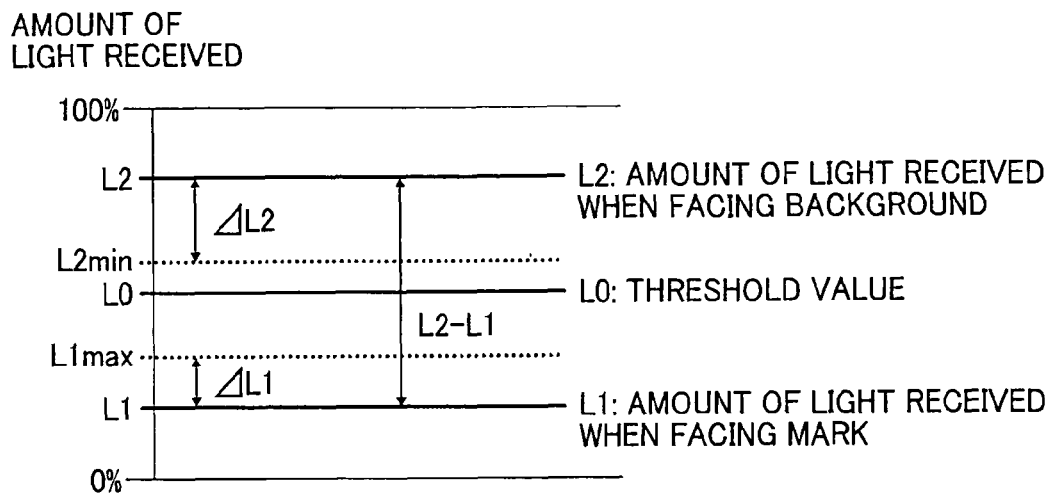
FIGS. 5A and 5B are graphs illustrating the levels L1 and L2 of the mark detection signals shown in FIGS. 4C1 and 4C2 and a threshold value level L0 used to binarize the levels.

L1 and L2 each include a fluctuation range due to the thickness of the web W and a variation during transport. The minimum value of L2 is represented by L2 min and the maximum value of L1 is represented by L1max. As shown in FIG. 5A, in the case where L1max<L2 min is satisfied, it is possible to discriminate the background and the mark if the threshold value (L0) for discriminating the background and the mark satisfies the following Conditional expression 1.

$$L1\max < L0 < L2\min \qquad (1)$$

In the case where the difference between L2 and L2min is ΔL2 and the difference between L1max and L1 is ΔL1, the difference L2−L1 between the received light amount data items may satisfy the following Conditional expression 2.

$$L2 - L1 > \Delta L1 + \Delta L2 \qquad (2)$$

The value of ΔL1+ΔL2 is stored as the determination value in the memory 53.

Figure 5B:
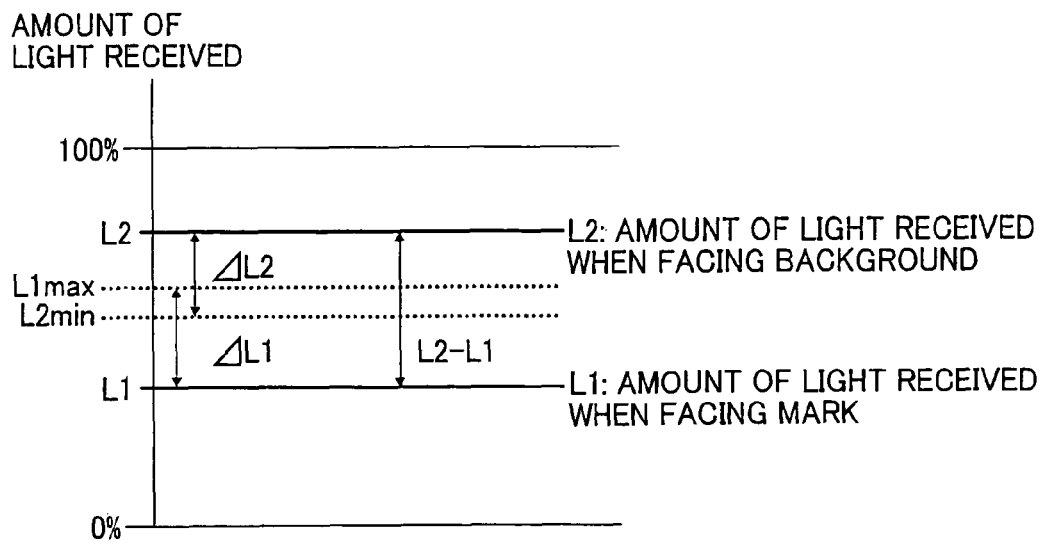

In FIG. 5A, since L1 and L2 satisfy Conditional expression 2, information indicating that the mounting angle (angle adjustment value) is appropriate is displayed on a display of the operation display board 54. In FIG. 5B in which the mounting angle is inappropriate and the difference between the mark received light amount data L1 and the background received light amount data L2 is small, L2−L1<ΔL1+ΔL2 is satisfied. In this case, it is difficult to discriminate the mark and the background, and information indicating that the mounting angle is inappropriate is displayed on the display of the operation display board 54. The process of adjusting the mounting angle, reading the received light amount data items L1 and L2, calculating the difference L2−L1, and comparing the difference with the determination value is performed again. In this way, by adjusting the mounting angle of the optical axis in such a manner that L1 and L2 satisfy. Conditional expression 2, it is possible to detect a positioning mark regardless of the kind of web.

Second Embodiment

In the first embodiment, as shown in FIGS. 2A and 2B, the slider 42 is mounted to the guide bar 46 such that the optical axes (target lines) of the light emission end 43 and the light receiving end 44 are placed on a plane perpendicular to the center line Ra. Therefore, as shown in FIG. 4D, the slider 42 is rotated in the direction in which the light emission end 43 and the light receiving end 44 are arranged, by the adjustment of the angle α. In a second embodiment, as shown in FIGS. 6A and 6B and FIGS. 7A1 to 7C, the slider 42 is mounted to the guide bar 46 such that the optical axes (aiming lines) of the light emission end 43 and the light receiving end 44 are placed on a plane including the (central axis of) guide bar 46 and the center line Ra of rotation. Therefore, in the second embodiment, as shown in FIG. 7C, the slider 42 is rotated in a direction perpendicular to the direction in which the light emission end 43 and the light receiving end 44 are arranged, by the adjustment of an angle β. In the second embodiment, the other structures are the same as those in the first embodiment. Similar to the first embodiment, it is possible to detect a positioning mark regardless of the kind of web by adjusting the mounting angle of the optical axis.

Figure 6A:
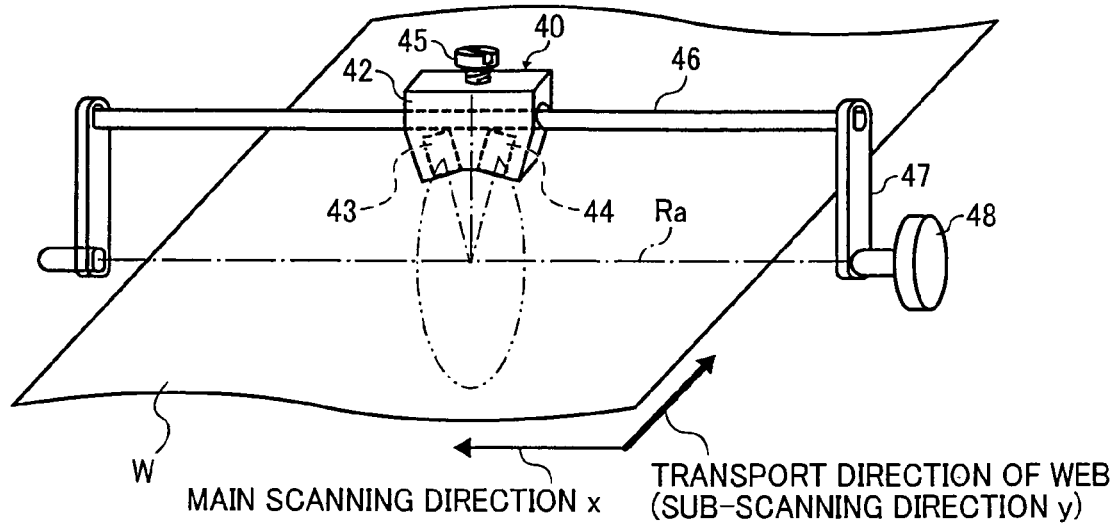
FIGS. 6A and 6B are enlarged perspective views illustrating the outline of an aiming angle adjusting mechanism that supports a detection end 40 of a mark detecting device according to a second embodiment of the invention.
Figure 6B:
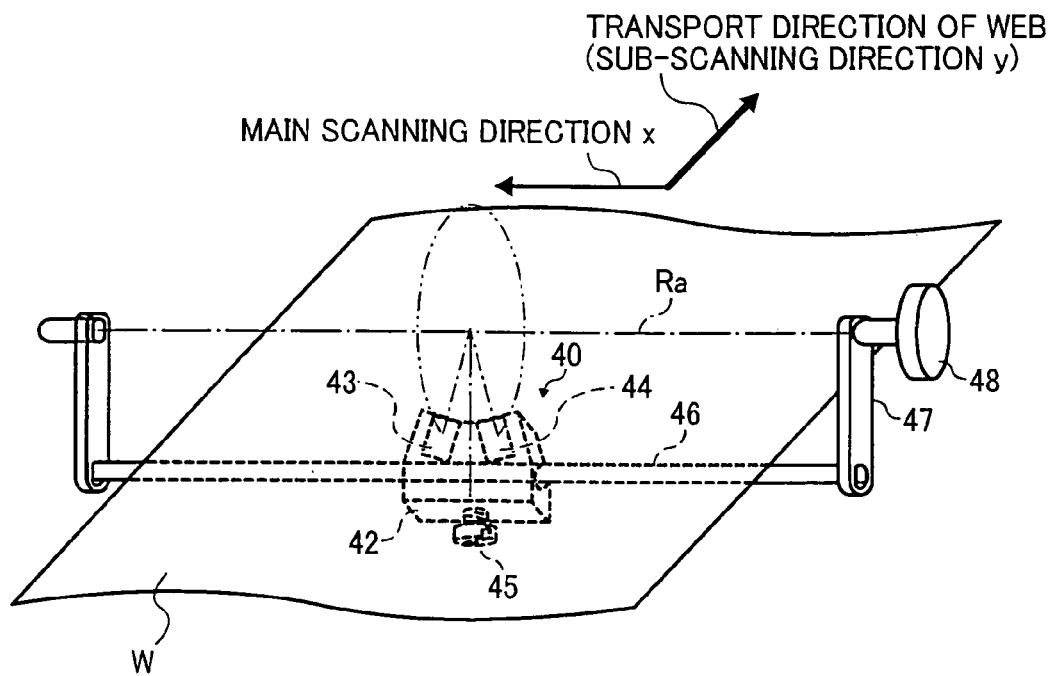

In the first and second embodiments, as shown in FIGS. 2A and 6A, the positioning mark formed on a surface opposite to the print surface is detected. However, the mounting angle correcting unit (the guide bar 46, the rotating arm 47, and the knob 48) may detect the positioning mark formed on the print surface, as shown in FIGS. 2B and 6B. In addition, the following structure may be used: the rotating arm 47 has a length that is two times more than that shown in FIGS. 2A and 2B and FIGS. 6A and 6B, the axial rod of the knob 48 is mounted at the center of the rotating arm, the first and second guide bars are supported by both ends of the rotating arm 47, and each of the guide bars includes the first and second sliders which are the same as the slider 42 shown in FIGS. 2A and 2B and FIGS. 6A and 6B. In this case, it is possible to simultaneously detect the marks on both sides of the web or selectively detect the mark on each surface.

When the fixing screw 45 is loosened, the slider 42 including the light emission end 43 and the light receiving end 44 can slide in the main scanning direction x. Therefore, the operator can manually adjust the position of the detection end 40 in the main scanning direction x. In this way, it is possible to correspond to the positions of various kinds of pre-print marks. In an aspect in which the adjustment is automatically performed, for example, a threaded rod that is driven by a motor is rotatably supported by the rotating arm 47 in parallel to the guide bar 46, and a nut into which the threaded rod is fitted and inserted is fixed to the slider 42. When the operator inputs an instruction to rotate the motor in the forward or backward direction to the operation display board 54, the slider 42 is moved forward and backward in the main scanning direction x.

The mounting angle correcting units 46 to 48 may be applied when the light emitting element of the optical sensor 49 is a single light source. This structure is effective for a web in which the background is white and a positioning mark or a pre-print pattern is a specific color. In addition, the light emitting element of the optical sensor 49 may include a plurality of light sources emitting different color light components. In this case, it is possible to improve the accuracy of detection when the background and the positioning mark or the pre-print mark are not specific colors.

In this way, it is possible to detect a positioning mark or a pre-print mark from various kinds of webs. Therefore, it is possible to obtain the effects of the invention even when the first and second printing apparatuses print different color images so as to be superimposed on each other or when printing is performed on a pre-printed web, as well as double-side printing.

According to the invention, the aiming angle adjusting unit (the guide bar 46, the rotating arm 47, and the knob 48) set the detection end 40 at a rotation angle where totally reflected light is not received in correspondence with the light reflection characteristics of the plane of a transfer medium W. Therefore, it is possible to accurately detect a positioning mark or a pre-printed mark on the transfer medium W, regardless of the kind of transfer medium W, such as whether the plane (for example, the surface of a web) of the transfer medium W is matte or glossy.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A mark detecting device that detects a positioning mark on a transfer medium based on light that is emitted to and then reflected from the transfer medium, the mark detecting device comprising:
   a light emitting unit that emits light to a target position on the transfer medium;
   a light receiving unit that receives light reflected from the target position; and
   an adjusting unit that rotatably supports a detecting unit including at least one of the light emitting unit and the light receiving unit about a center of rotation, which passes through the target position, on the transfer medium and adjusts the rotation angle of the detecting unit with respect to the center of rotation, wherein the adjusting unit includes:
      a rotating arm having one end that is rotated about the center of rotation; and
      a supporting portion that is supported by a free end of the rotating arm and supports the detecting unit.

2. The mark detecting device according to claim 1, wherein the supporting portion includes a guide bar that extends in a main scanning direction perpendicular to a transport direction of the transfer medium.

3. The mark detecting device according to claim 2, wherein the detecting unit is slidable in the main scanning direction with respect to the guide bar.

4. The mark detecting device according to claim 1, further comprising:
   a verifying unit that verifies whether the adjusted rotation angle is appropriate on the basis of an amount of reflected light received when the positioning mark is detected and an amount of reflected light received when a background is detected.

5. The mark detecting device according to claim 4, wherein the verifying unit judges that the rotation angle is appropriate when an absolute value of a difference between the amount of the reflected light received when the positioning mark is detected and the amount of the reflected light received when the background is detected is more than a determination value.

6. The mark detecting device according to claim 4, further comprising:
   a notifying unit that notifies the verification result of the verifying unit.

7. The mark detecting device according to claim 1,
wherein the adjusting unit rotatably supports the detecting unit on a front side of the transfer medium about the center of rotation.

8. The mark detecting device according to claim 1,
wherein the adjusting unit rotatably supports the detecting unit on a rear side of the transfer medium about the center of rotation.

9. An adjustment method performed in a mark detecting device that detects a positioning mark on a transfer medium based on light that is emitted to and then reflected from the transfer medium, the adjustment method comprising:

rotatably supporting a detecting unit on an adjusting unit that includes a rotating arm having one end that is rotated about a center of rotation and a supporting portion that is supported by a free end of the rotating arm and supports the detecting unit, the detecting unit including at least one of a light emitting unit that emits light to a target position on the transfer medium and a light receiving unit that receives light reflected from the target position about the center of rotation, which passes through the target position, on the transfer medium and adjusting the rotation angle of the detecting unit with respect to the center of rotation.

10. A printing apparatus comprising:
a mark detecting device that detects a positioning mark on a transfer medium based on light that is emitted to and then reflected from the transfer medium;
an image forming unit that forms an image on the transfer medium;
a transport unit that transports the transfer medium to the image forming unit; and
a transport control unit that changes transport speed of the transfer medium to the image forming unit by the transport unit on the basis of the positioning mark,
wherein the marking detecting device includes
a light emitting unit that emits light to a target position on the transfer medium;
a light receiving unit that receives light reflected from the target position; and
an adjusting unit that rotatably supports a detecting unit including at least one of the light emitting unit and the light receiving unit about a center of rotation, which passes through the target position, on the transfer medium and adjusts the rotation angle of the detecting unit with respect to the center of rotation, wherein the adjusting unit includes:
a rotating arm having one end that is rotated about the center of rotation; and
a supporting portion that is supported by a free end of the rotating arm and supports the detecting unit.

\* \* \* \* \*